United States Patent
Tanaka et al.

(10) Patent No.: US 6,709,670 B1
(45) Date of Patent: Mar. 23, 2004

(54) AMINOETHANESULFONIC ACID-CONTAINING PREPARATIONS

(75) Inventors: Toshiki Tanaka, Wakayama (JP); Yasushi Furuta, Arida (JP)

(73) Assignee: Nippon Chemical Works Co., Ltd., Wakayama (JP)

( * ) Notice: Subject to any disclaimer, the term of this patent is extended or adjusted under 35 U.S.C. 154(b) by 122 days.

(21) Appl. No.: 10/019,281

(22) PCT Filed: Jun. 22, 2000

(86) PCT No.: PCT/JP00/04100

§ 371 (c)(1),
(2), (4) Date: Jan. 2, 2002

(87) PCT Pub. No.: WO01/01982

PCT Pub. Date: Jan. 11, 2001

(30) Foreign Application Priority Data

Jul. 2, 1999  (JP) ............................................ 11-188348

(51) Int. Cl.⁷ ........................... A61F 13/02; A61L 9/04; A61K 9/14; A61K 9/68; A61K 9/20
(52) U.S. Cl. .................. 424/434; 424/435; 424/45; 424/46; 424/48; 424/439; 424/441; 424/464; 424/465
(58) Field of Search .......................... 424/48, 439, 441, 424/464, 465, 45, 46, 434, 435

(56) References Cited

FOREIGN PATENT DOCUMENTS

| EP | 1 199 073 | | 4/2002 |
|---|---|---|---|
| JP | 6-501954 A | * | 3/1994 |
| JP | 6-501954 | | 3/1994 |
| JP | 8-99849 A | * | 4/1996 |
| JP | 8-99849 | | 4/1996 |
| JP | 10-109931 | | 4/1998 |
| JP | 10-175856 | | 6/1998 |
| JP | 11-60476 A | * | 3/1999 |
| JP | 11-60476 | | 3/1999 |
| WO | WO 92/17170 | | 10/1992 |

OTHER PUBLICATIONS

Patent Abstracts of Japan, JP 11–60476, Mar. 2, 1999.
Patent Abstracts of Japan, JP 8–99849, Apr. 16, 1996.
Patent Abstracts of Japan, JP 10–109931, Apr. 28, 1998.
Patent Abstracts of Japan, JP 10–175856, Jun. 30, 1998.

* cited by examiner

*Primary Examiner*—Carlos A. Azpuru
(74) *Attorney, Agent, or Firm*—Oblon, Spivak, McClelland, Maier & Neustadt, P.C.

(57) ABSTRACT

Preparations to be applied to the oral or nasal cavity which contain aminoethanesulfonic acid and a mucosal stimulant. When these preparations are applied to the oral or nasal cavity, aminoethanesulfonic acid can be quickly and efficiently absorbed via the activated oral or nasal mucosa. The administration of these preparations quickens recovery from fatigue.

19 Claims, No Drawings

AMINOETHANESULFONIC ACID-CONTAINING PREPARATIONS

This application is a 371 continuation of PCT/JP00/04100 filed Jun. 22, 2000.

TECHNICAL FIELD

This invention relates to an aminoethanesulfonic acid-containing preparation. More particularly, the invention relates to the preparation to be absorbed via the oral or nasal mucosa with a noticeably increased absorption rate of aminoethanesulfonic acid (drug name: "Taurine") in the body. The present invention also relates to a method for absorbing aminoethanesulfonic acid via the oral or nasal mucosa, as well as a method for quick recovery from fatigue, using the said preparation.

BACKGROUND ART

Aminoethanesulfonic acid has been known to activate cells and strengthen various organs such as cardiac muscle, cholecyst or liver, and thus to be effective for keeping skin healthy and beautiful and preventing a hangover. Moreover, the acid is said to have an arteriosclerosis-preventing action, because it promotes secretion of bile, increases digestion and absorption of fats and fat-soluble vitamins and inhibits bad cholesterol.

Various kinds of aminoethanesulfonic acid-containing preparations such as injections, drinkable preparations, tablets or powders are now on the market, relying on the development of excellent actions of aminoethanesulfonic acid as depicted above.

Apart from the injections for medicinal purpose, other preparations are intended for oral administration in which aminoethanesulfonic acid is absorbed via the digestive tracts such as the stomach or the intestines.

A considerably longer time is needed for absorption of aminoethanesulfonic acid via the gastrointestinal tracts. Moreover, aminoethanesulfonic acid is unstable to strong acids such as gastric juice or other digestive juices, owing to the primary amino group involved therein, and absorption efficiency of the acid is not satisfactory. With more quick and increased absorption of aminoethanesulfonic acid, one can expect a quick recovery from fatigue after hard exercise or long-range desk work or an earlier recovery of hangover or drunken sickness after heavy drinking.

An object of the present invention is to provide an aminoethanesulfonic acid-containing preparation having an improved absorption rate and absorption efficiency in the body.

DISCLOSURE OF THE INVENTION

We have made our earnest studies to accomplish the above-mentioned object and, as a result, noticed that absorption rate and absorbed amount of aminoethanesulfonic acid is remarkably increased by absorbing it via the oral or nasal mucosa which have been activated by a mucosal stimulant, upon which the invention has been completed.

This invention is directed to a preparation to be applied to the oral or nasal cavity which contains aminoethanesulfonic acid and a mucosal stimulant.

The preparation may include a preparation which contains spices as a mucosal stimulant; it also includes a preparation in the form of chewing gums, troches, pills or aqueous sprays.

This invention includes a method for absorbing aminoethanesulfonic acid in the body via the oral or nasal mucosa by administering the above-mentioned preparation.

The invention further includes a method for quick recovery of fatigue by applying the above-mentioned preparation to the oral or nasal cavity.

BEST MODE FOR CARRYING OUT THE INVENTION

The preparation to be applied to the oral or nasal cavity according to the present invention contains aminoethanesulfonic acid and a mucosal stimulant.

Aminoethanesulfonic acid is one of physiologically active substances found in mammals, fish, mollusks and others, which is represented by the general formula $H_2NCH_2CH_2SO_3H$, and which has been marketed in the generic drug name of "Taurine".

The mucosal stimulant is a substance approved as a medicine or food additive, which may stimulate the oral or nasal mucosa to facilitate the blood flow in the intramucosal or submucosal capillaries, and which would not adversely affect a human body. Mucosal stimulants may include spices or herbs; bitters comprising, for example, sodium, potassium, calcium or magnesium salts; natural or synthetic sweeteners such as sucrose, fructose, glucose, milk sugar, sorbitol, maltose, lactose or saccharin sodium; sour substances such as citric acid, malic acid, tartaric acid, fumaric acid, acetic acid or cinnamic acid; flavors comprising esters of such sour substances; aromatic substances such as 1-menthol, anethole, eugenol, cineole, methyl salicylate, spearmint oil, peppermint oil, lemon oil or orange oil; and activating substances such as ethanol or glycerol.

The preparation according to the invention comprises at least one of these mucosal stimulants, preferably several of them.

The dosage forms of the present preparation are not particularly critical, but they may be preferably of the dosage form which could retain the preparation in the oral or nasal cavity as long as possible without swallowing at one gulp. As preparations to be applied to the oral cavity, there may be mentioned, for example, pills (taffies or candies), chewing gums, troches, sublingual tablets, sprays and the like, and chewing gums are particularly preferred. As preparations to be applied to the nasal mucosa, there may be mentioned sprays.

The preparations according to the invention may further contain other additives such as dyes, coloring agents, preservatives, penetrating agents, pH adjusters and the like, as required. There may be also incorporated necessary binding agents, excipients, disintegrating agents, lubricants, gum bases, fillers, emulsifying agents and the like, depending on the dosage forms.

Typically, sugar and starch syrup may be used for candy-like pills. For troches or sublingual tablets, there may be used binding agents such as microcrystalline cellulose, acacia, tragacanth gum or gelatin; excipients such as starch, lactose or carboxymethylcellulose; disintegrating agents such as alginic acid, primogel (sodium starch glycolate) or corn starch; lubricants such as magnesium stearate or stetrotex (hydrogenated vegetable oil); glidants such as colloidal silicon dioxide. For chewing gum preparations, there may be used gum base materials such as chicle, jelutong (jelutong gum), sorva (sorva latex), vinyl acetate resins or natural wax, e.g., rice wax, carnaba wax or micro wax; fillers such as calcium carbonate or talc; emulsifying agents such as fatty acid glycerol esters or sugar esters. In addition to water, pH adjusters, solution-stabilizers or sol-stabilizers may be used for sprays for which aerosol forms or pump spraying systems may be adopted.

By applying the preparation according to the invention to the oral or nasal cavity, aminoethanesulfonic acid may be rapidly transferred into blood capillaries and thereafter into the cardiovascular system via the oral or nasal mucosa which has been activated by the action of the mucosal stimulant prior to swallowing. In applying the preparation of the invention to the oral or nasal cavity, in particular, the oral cavity, absorption efficiency of aminoethanesulfonic acid may be increased by retaining it in the oral cavity over a certain period of time without swallowing at one gulp.

For recovery from physical fatigue after exercise or eyestrain caused by desk work, the preparation of the invention may be applied to the oral or nasal cavity to achieve quick recovery from physical fatigue or sleepiness. Also, the said preparation may be applied for sobering up or for the purpose of beauty or medical care.

EXAMPLES

The present invention will be more fully illustrated by way of the following examples. In the examples, "part" is part by weight.

Example 1

Transfer Rate of Aminoethanesulfonic Acid Into Blood (i) Test Chewing Gums

Chewing gum (a): Gum containing 1.0 g of aminoethanesulfonic acid in the total amount of 5.0 g.

The chewing gum (a) was prepared by incorporating 1.0 part of aminoethanesulfonic acid into 4.0 parts of a gum base comprising vinyl acetate as a main component. Chewing gum (b): Gum containing 1.0 g of aminoethanesulfonic acid in the total amount of 5.1 g.

The chewing gum (b) was prepared by incorporating 1.0 part of aminoethanesulfonic acid and 0.1 part of grained red chili pepper into 4.0 parts of a gum base comprising vinyl acetate as a main component.

Chewing gum (c): Gum containing 1.0 g of aminoethanesulfonic acid in a total amount of 5.65 g.

The chewing gum (c) was prepared by incorporating 1.0 part of aminoethanesulfonic acid, 0.05 part of menthol, 0.1 part of cinnamon and 1.5 parts of cane sugar into 3.0 parts of a gum base comprising vinyl acetate as a main component.

(ii) Determination of Concentration of Aminoethanesulfonic Acid Transferred Into Blood Three adults, A, B and C of a similar build, each weighing approximately 65 kg were fasted for 12 hours. Then, their blood were collected, which were immediately subjected to amino acid analysis using an amino acid autoanalyzer (JLC-300V, manufactured by JEOL). After the blood collection, Adult A fully chewed the test chewing gum (a) while moving it inside the mouth using his tongue for 30 minutes, Adult B did the test chewing gum (b) and Adult C did the test chewing gun (c), in the same manner. During this period, saliva was kept within the mouth without swallowing. After 30 minutes, the gum and saliva were spit out, and the mouth was rinsed out with drinking water, which was then split out from the mouth. After 20 minutes, the blood were again collected and subjected to amino acid analysis.

Table 1 shows aminoethanesulfonic acid (Taurine) concentrations in the blood of the three adults before and after application of the test chewing gums as well as the differences between the two concentrations.

TABLE 1

Concentrations of aminoethanesulfonic acid transferred into blood

| | | | Taurine concentration in blood (nmol/ml) | | |
|---|---|---|---|---|---|
| No. | Adult | Gum | Before appln.*) | After appln. | Difference between before and after applns. |
| 1-A | A | (a) | 95.5 | 122.0 | 26.5 |
| 1-B | B | (b) | 89.1 | 234.4 | 145.3 |
| 1-C | C | (c) | 111.7 | 275.9 | 164.2 |

*)appln = application

As is apparent from Table 1, in the cases (1-B and 1-C) where the chewing gums containing the mucosal stimulants are applied, the aminoethanesulfonic acid concentrations before and after applications were remarkably higher as compared with the control case (1-A) where no mucosal stimulant was incorporated. This indicates that the presence of the mucosal stimulant could remarkably increase the absorption rate of aminoethanesulfonic acid.

Example 2

Chewing Gum Preparations

| | |
|---|---|
| Aminoethanesulfonic acid | 20.0 parts |
| Japanese basil | 2.0 parts (equivalent to 0.002 part of perilla oil) |
| Ginger | 0.1 part (equivalent to 0.01 part of essential oil) |
| Menthone | 0.01 part |
| 1,8-Cineol | 0.1 part |
| Anethole | 0.08 part |
| Menthol | 0.5 part |
| Carvone | 0.1 part |
| Methyl salicylate | 0.05 part |
| Cane sugar | 48.0 parts |
| Starch syrup | 7.0 parts |
| Gum base | 22.0 parts |

(chicle, sorva, natural gum, vinyl acetate resin, ester gum, micro wax, calcium carbonate and fatty acid monoglyceride blended in proper amounts)

The above materials were placed into a kneader and kneaded well to prepare a base material and then the material was extruded from an extruder. The extruded stock was shaped into a sheet with a given thickness by means of pressure rolls and then cut to prepare the chewing gum preparations.

Example 3

Troches to be Applied to the Oral Cavity

| | |
|---|---|
| Aminoethanesulfonic acid | 30.0 parts |
| Zanthoxylum | 1.0 part |
| Cinnamon | 0.5 part |
| Mint oil | 0.6 part |
| Turmeric | 0.1 part |
| Sucrose | 65.0 parts |
| Hydroxypropylcellulose | 0.5 part |
| Magnesium stearate | 2.0 parts |

The above materials were admixed and direct-compressed to prepare oral troches, each weighing 1.4 g.

Example 4

Troches to be Applied to the Oral Cavity

| | |
|---|---|
| Aminoethanesulfonic acid | 35.0 parts |
| Capsaicine | 0.2 part |
| Acacia | 3.0 parts |
| Glucose | 50.0 parts |
| Gelatin | 2.0 parts |
| Flavor | 0.1 part |
| Water | 10.0 parts |

The above materials were admixed and direct-compressed to prepare oral troches, each weighing 1.4 g.

Example 5

Aqueous Sprays

Two pieces of red chili pepper were boiled in 1000 ml of water for 4 minutes and then allowed to cool down to 80° C. At this point, 100 g of aminoethanesulfonic acid was dissolved therein while the pieces of red chili pepper were taken away. The resulting solution was cooled to room temperature, and then 8 g of ethanol, 5 g of glycerol, 100 g of cane sugar and a small amount of flavor were added to prepare an aqueous preparation of aminoethanesulfonic acid containing capsaicine. The preparation was charged into a pump-sprayable vessel to prepare a spray.

Example 6

Aqueous Sprays

In 80.0 parts of purified water was dissolved 8.0 parts of aminosulfoic acid by warming and to the resulting solution were added 0.8 part of ethanol, 0.5 part of glycerol, 0.8 part of malic acid, 10.0 parts of cane sugar and a small amount of mint oil and flavor to prepare an aqueous preparation. The preparation was charged into a pump-sprayable vessel to prepare a spray.

Example 7

Pills (Candy-like Preparations)

Sugar and starch syrup were admixed in equal amounts and molten by heating. To the molten product was added aminoethanesulfonic acid in an amount of 25% by weight of the total amount and then the mixture was further boiled down. Thereafter, 0.2% by weight of capsaicine and 1% by weight of ground ginger, each based on the total amount, were further added, and the candy-like preparations were prepared according to a conventional method.

Industrial Applicability

The present invention provides an aminoethanesulfonic acid-containing preparation having remarkably improved absorption rate and absorption efficiency of aminoethanesulfonic acid. Intramucosal and submucosal blood circulation can be promoted by the action of the mucosal stimulant incorporated in the preparation and, as a result, absorption rate of aminoethanesulfonic acid via the oral or nasal mucosa is remarkably increased.

The invention further provides a method for rapidly absorbing aminoethanesulfonic acid using the said preparation, as well as a method for quick recovery from fatigue by applying the said preparation to the oral or nasal cavity.

What is claimed is:

1. A preparation for administration to the oral or nasal cavity, comprising aminoethanesulfonic acid and at least one spice or extract thereof selected from the group consisting of red chili pepper, Japanese basil, ginger and zanthoxylum.

2. The preparation as claimed in claim 1 in the form of a chewing gum, a troche, a pill or an aqueous spray.

3. The preparation as claimed in claim 1, comprising red chili pepper or an extract thereof.

4. The preparation as claimed in claim 1, comprising Japanese basil or an extract thereof.

5. The preparation as claimed in claim 1, comprising ginger or an extract thereof.

6. The preparation as claimed in claim 1, comprising zanthoxylum or an extract thereof.

7. The preparation as claimed in claim 1, comprising 1 part by weight of aminoethanesulfonic acid and 0.1 parts by weight of the spice or extract thereof.

8. The preparation as claimed in claim 1, wherein the aminoethanesulfonic acid and the spice or extract thereof are present in a ratio of 10:1 in parts by weight.

9. The preparation as claimed in claim 1, comprising at least one extract of red chili pepper, Japanese basil, ginger, or zanthoxylum.

10. The preparation as claimed in claim 9, wherein the extract is obtained by boiling the spice in water, then separating the water from the pieces of spice.

11. The preparation as claimed in claim 1, comprising at least one of perilla oil or capsaicine.

12. A method comprising applying the preparation as claimed in claim 1 to an oral or nasal cavity.

13. The method as claimed in claim 12, wherein the preparation is applied to a human.

14. The method as claimed in claim 12, wherein the preparation is applied in an amount effective for increasing the aminoethanesulfonic acid concentration in the blood of a human.

15. The method as claimed in claim 12, wherein the preparation is applied to the oral cavity of a human.

16. The method as claimed in claim 12, wherein the preparation is applied to the nasal cavity of a human.

17. The method as claimed in claim 12, wherein the spice or extract thereof is present in an amount effective for increasing the absorption rate of aminoethanesulfonic acid to the blood of a human.

18. The method as claimed in claim 12, wherein the preparation is applied to the nasal cavity in the form of a spray.

19. The method as claimed in claim 12, wherein the preparation is applied to the oral cavity in the form of a chewing gum preparation, a troche or a pill.

* * * * *